United States Patent
Tsaur et al.

(10) Patent No.: US 8,124,574 B2
(45) Date of Patent: *Feb. 28, 2012

(54) MILD, FOAMING LIQUID CLEANSERS COMPRISING LOW LEVELS OF FATTY ISETHIONATE PRODUCT AND LOW TOTAL FATTY ACID AND/OR FATTY ACID SOAP CONTENT

(75) Inventors: Liang Sheng Tsaur, Norwood, NJ (US); Virgilio Barba Villa, Emerson, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 12/577,425

(22) Filed: Oct. 12, 2009

(65) Prior Publication Data

US 2011/0086789 A1    Apr. 14, 2011

(51) Int. Cl.
A61K 7/50    (2006.01)

(52) U.S. Cl. ........ 510/130; 510/156; 510/424; 510/426; 510/492; 510/490

(58) Field of Classification Search .......................... None
See application file for complete search history.

(56) References Cited

U.S. PATENT DOCUMENTS

| | | |
|---|---|---|
| 3,723,325 A | 3/1973 | Parran, Jr. |
| 4,565,647 A | 1/1986 | Llenado |
| 5,009,814 A | 4/1991 | Kelkenberg et al. |
| 5,132,037 A | 7/1992 | Greene et al. |
| 5,234,619 A | 8/1993 | Greene et al. |
| 5,290,471 A | 3/1994 | Greene et al. |
| 5,372,751 A | 12/1994 | Rys-Cicciari et al. |
| 5,389,279 A | 2/1995 | Au et al. |
| 5,415,810 A | 5/1995 | Lee et al. |
| 5,612,307 A | 3/1997 | Chambers et al. |
| 5,716,919 A | 2/1998 | Sano |
| 5,739,365 A | 4/1998 | Briody et al. |
| 5,804,540 A | 9/1998 | Tsaur et al. |
| 5,952,286 A | 9/1999 | Puvvada et al. |
| 5,965,500 A | 10/1999 | Puvvada |
| 6,077,816 A | 6/2000 | Puvvada et al. |
| 6,429,177 B1 | 8/2002 | Williams et al. |
| 7,084,104 B2 | 8/2006 | Martin et al. |
| 7,098,180 B2 | 8/2006 | Ganopolsky et al. |
| 7,119,059 B2 | 10/2006 | Librizzi et al. |
| 7,655,607 B2 | 2/2010 | Tsaur et al. |
| 7,659,235 B2 | 2/2010 | Tsaur et al. |
| 7,671,000 B2 | 3/2010 | Tsaur et al. |
| 7,674,759 B2 | 3/2010 | Tsaur |
| 7,807,612 B2 | 10/2010 | Tsaur |
| 2004/0224863 A1 | 11/2004 | Sun et al. |
| 2005/0075256 A1 | 4/2005 | Librizzi et al. |
| 2005/0100570 A1 | 5/2005 | Wei et al. |
| 2005/0136026 A1 | 6/2005 | Qiu |
| 2005/0143268 A1 | 6/2005 | Midha et al. |
| 2005/0192188 A1 | 9/2005 | Wagner et al. |
| 2006/0079420 A1 | 4/2006 | Wagner et al. |
| 2009/0156450 A1* | 6/2009 | Tsaur ........................... 510/129 |

FOREIGN PATENT DOCUMENTS

| | | |
|---|---|---|
| EP | 0 559 375 A1 | 9/1993 |
| EP | 1029532 | 8/2000 |
| EP | 1 479 365 | 11/2004 |
| EP | 1237534 | 1/2005 |
| GB | 2 015 561 A | 9/1979 |
| WO | 97/05957 | 2/1997 |
| WO | 99/32069 | 7/1999 |
| WO | 00/21492 | 4/2000 |
| WO | 03/017968 | 3/2003 |
| WO | 2008/074617 | 6/2006 |
| WO | 2006/077495 A2 | 7/2006 |
| WO | 2009/030594 A1 | 3/2009 |

OTHER PUBLICATIONS

PCT Search Report on International Application No. PCTIEP2007/063128 dated Apr. 15, 2008.
PCT Search Report on International Application No. PCT/EP2008/067530 dated Jul. 24, 2009.
PCT Search Report on International Application No. PCT/EP2008/060835 dated Jan. 26, 2009.
PCT Search Report and Written Opinion for Internationai Application No. PCT/EP2009/062278 dated Sep. 22, 2009.
XP-002474464, Oct. 1988, Engiish translation of JP 1987-0077976 (based on JP 63-243200).
Co-pending application for: Applicant: Tsaur et al.; U.S. Appl. No. 12/235,955, filed Sep. 23, 2008; entitled: Stable cleansing compositions containing fatty acyl isethionoate surfactant products having more than 10 wt. % of fatty acid/fatty soap content using high level of polyol and methods thereof.
Co-pending application for: Applicant: Tseur et al.; U.S. Appl. No. 12/751,049, filed Mar. 31, 2010: entitled: Personal wash cleanser with mild surfactant systems comprising defined alkartoyi compounds and defined fatty acyl isethionate surfactant product.
Co-pending application for: Applicant: Tsaur et al.; U.S. Appl. No. 12/751,063, flied Mar. 31, 2010; entitled Personal wash cleanser comprising defined alkanoyl compounds, defined fatty acyl isethionate surfactant product and skin of hair benefit agent.
Co-pending application for: Applicant: Tsaur et al.; U.S. Appl. No. 12/751,079, filed Mar. 31, 2010; entitled: Personal wash cleanser comprising defined alkanoyl compounds, defined fatty acyl isethionate surfactant product and skin or hair benefit a ant delivered in flocs upon dilution.
PCT International Search Report and Written Opinion on Application No. PCT/EP2010/064629 dated Apr. 27, 2011.

* cited by examiner

*Primary Examiner* — Necholus Ogden, Jr.
(74) *Attorney, Agent, or Firm* — Ronald A. Koatz

(57) ABSTRACT

The present invention relates to liquid personal care composition comprising both low levels of specific fatty isethionate product (e.g., less than 4%) and low overall fatty acid content (less than 4%) which, quite surprisingly, maintain excellent foaming profile relative to identical composition having high overall fatty acid content.

2 Claims, No Drawings

MILD, FOAMING LIQUID CLEANSERS COMPRISING LOW LEVELS OF FATTY ISETHIONATE PRODUCT AND LOW TOTAL FATTY ACID AND/OR FATTY ACID SOAP CONTENT

FIELD OF THE INVENTION

The present invention is directed to liquid personal care skin or hair cleansing compositions comprising low levels of specific fatty isethionate product (e.g., less than 4% by wt., preferably less than 3% by wt.) and low overall fatty acid/fatty acid soap content (e.g., less than 4%). Surprisingly and unpredictably, both low fatty isethionate product and low total fatty acid/soap are required to maintain superior lather relative to compositions otherwise identical or substantially identical (e.g., with regard to surfactants, emollients, polymers) except that they have higher overall fatty acid/fatty acid soap content (e.g., greater than 4%) or higher fatty isethionate product. Amounts of long chain fatty acid/soap in the fatty isethionate product have been found critical for good mildness. Total amount of fatty acid/soap in the product are also critical.

BACKGROUND OF THE INVENTION

Fatty acyl isethionates (e.g., cocoyl isethionates) are anionic surfactants highly desirable in personal care skin or hair cleansing products, particularly in personal care products, because they lather well, are generally mild to the skin and have good emollient properties. Typically, fatty acid isethionates are produced by esterification of fatty acids or by reaction of fatty acid chloride having carbon chain length of $C_8$ to $C_{20}$ with isethionate. A typical fatty acyl isethionate surfactant product (e.g., commercially sold or made surfactant product) contains about 40 to 95 wt. % fatty acyl isethionate, and 0 to 50 wt. %, typically 5 to 40 wt. % free fatty acid, in addition to isethionate salts, typically at less than 5%, and trace amounts (less than 2 wt. %) of other impurities. In the present invention, since low total amounts of isethionate product are used, it has been found critical that there be present minimum levels (greater than 15%, preferably greater than 20%) of fatty acid/fatty soap, as percent of the product, and in addition, that greater than 50% preferably greater than 60% of these fatty acid/soaps in the product be of chain length $C_{16}$-$C_{20}$ (e.g., to preserve mildness). Specifically levels of long chain in the product (calculated by multiplying total fatty acid/soap in the product by the % of long chain) should be greater than 7.5%, preferably greater than 10%.

In a previous application, U.S. Ser. No. 11/958,471, applicants claimed the use of compositions comprising 3 to 45% by wt. fatty acyl isethionate product and 4 to 20% by wt. $C_8$ to $C_{20}$ total linear fatty acids and/or fatty soaps in the total composition. By ensuring that fatty acids/fatty acid soaps of a length of greater than $C_{14}$ comprise 20 to 70% of total linear fatty acid/fatty acid soap and that ratio of total linear fatty acid/fatty soap to total synthetic surfactant was within defined ranges, applicants in that application were able to ensure consistent viscosity at both high and low temperatures.

That application was particularly concerned with utilizing fatty acyl isethionate products which might contain relatively large levels (e.g., at least 10% of product) of free fatty acid.

In that reference, never was there used less than 4% by wt. of a fatty acid isethionate product (4% used in Example 13) and in that example, there was also used at least 4% free fatty acid (e.g., 4% lauric acid) and certainly more since there is also some fatty acid present in the fatty acyl isethionate product itself.

It was never contemplated to use low levels of acyl isethionate product and low levels of total fatty acid because the expectation of one skilled in the art would be that use of less fatty acyl isethionate product would lead to lower foam values. Quite unpredictably, however, applicants have found that it is possible to use lower levels of fatty acyl isethionate product (maintaining benefits of such products at lower cost) while retaining good foam, but only if the level of total free fatty acid/fatty soap is maintained below 4% and the total level of $C_{16}$ to $C_{20}$ fatty acid/fatty soaps is in the range of 0.1 to 2%, preferably 0.3 to 1.5% in order to provide both mildness and good lather. Thus, counterintuitively, applicants are able to use both less acyl isethionate product and less free fatty acid (indeed unpredictably applicants have found they must use less fatty acid) in order to ensure good foaming.

Applicants are aware of no reference in the art which teach or suggest low levels of acyl isethionate product in combination with ceiling levels of free fatty acid/soap (from combined acyl isethionate product and free fatty acid/soap in total composition) in order to ensure superior foaming relative to otherwise identical compositions having higher total free fatty acid/soap.

Other references which may be broadly related include: U.S. Pat. No. 5,415,810 to Lee; U.S. Pat. No. 5,739,365 to Brody; U.S. Publication No. 2004/0274863; U.S. Pat. Nos. 5,952,286 and 6,077,816 to Puwada; U.S. Pat. Nos. 5,132, 037, 5,234,619 and 5,290,471 to Greene et al.

Applicants have also filed, in addition to U.S. Ser. No. 11/958,471 noted above, additional applications in this general area as noted:
Ser. No. 11/613,617
Ser. No. 11/613,696
Ser. No. 11/613,666
Ser. No. 11/850,159
Ser. No. 12/235,955.

As indicated, none of the references discloses 0.1 to less than 4%, preferably 0.5 to less than 4%, preferably 0.5 to 3.8% by wt. fatty acid isethionate product which must be used in combination with 0.1 to less than 4%, preferably 0.3 to 3.8% total free fatty acid/soap (from combined product and free fatty acid/soap); and where the total amount of long chain $C_{16}$ to $C_{20}$ fatty acid/soap is in the range of 0.1 to 2%, preferably, 0.3 to 1.5% in the liquid composition of the invention. Moreover, none of the references recognizes that, only when total free fatty acid/soap is maintained at these levels will foam be unexpectedly enhanced in otherwise identical (e.g., in terms of co-surfactant, emollient, cationic polymer, etc.) compositions. This is counterintuitive because one would want to use more of fatty acid isethionate product to enhance foam.

As indicated, applicants have been able to achieve this goal at least in part (while retaining good mildness) by utilizing isethionate products which have relatively large amounts of free fatty acid/soap (greater than 15%) of which $C_{16}$ to $C_{20}$ comprise >50% such that total levels of long chain length is greater than 7.5% preferably greater than 10% of the product.

BRIEF SUMMARY OF THE INVENTION

The present invention is directed to novel liquid cleansing composition comprising both less than 4% fatty isethionate product and less than 4%, preferably less than 3.8% total fatty acid/soap simultaneously. it is unpredictable and quite unexpected that when both these parameters are present at levels below 4%, the level of foam (in otherwise identical compositions) is significantly higher relative to foam level of compositions where either level of isethionate product is greater than or equal to 4% and/or level of total fatty acid/fatty acid soap is greater than or equal to 4%. Further, both the total level of fatty acid/soap in the product and the amount of long chain fatty acid/soap in the isethionate product component has been found critical.

More specifically, the subject invention comprises liquid cleansing composition comprising:

(a) 0.3 to less than 4% fatty acid isethionate product, wherein said product comprises 40 to 80% fatty acyl isethionate as well as 15 to 50%, preferably greater than or equal to 20% to 50% of free fatty acids and/or fatty soaps in that product and wherein (e.g., to ensure mildness of final composition) greater than 20%, preferably greater than 25% of the fatty acyl isethionate are of chain length greater than or equal to $C_{16}$, and greater than 50%, preferably greater than 60% of the free fatty acid/soap are of chain length $\geq C_{16}$ (e.g., $C_{16}$ to $C_{24}$, preferably $C_{16}$ to $C_{20}$);

(b) 3 to 15% preferably 5 to 15% by wt. of a co-surfactant selected from the group consisting of anionic surfactant (excluding fatty acyl isethionate component of the fatty acyl isethionate product of (a)), amphoteric surfactant, nonionic surfactant and mixtures thereof;

(c) 0.1 to less than 4% $C_8$ to $C_{20}$ total linear free fatty acids/fatty soaps (comprising both free fatty acids/fatty soaps in the fatty acyl isethionate product of (a) as well as those added separately in composition) wherein the total amount of linear $C_{16}$ to $C_{20}$ fatty acids is less than 2%, preferably less than 1.5%, but at least 0.1%, preferably 0.3%.

Preferably, the ratio of fatty acyl isethionate surfactant of item (a) to total synthetic surfactants in item (b) is less than ½, preferably less than ⅓

Preferably, foam volume (measured by cylinder shake method) at fatty acid/soap level less than 4% is better by at least about 10%, preferably about 15% relative to identical composition comprising greater than or equal to 4% fatty acid/soap.

pH of the compositions typically is from about 4.5 to 7.6, preferably 5.0 to 7.2.

In a second embodiment, the invention relates to a process for making such composition.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Further in specifying the range of concentration, it is noted that any particular upper concentration can be associated with any particular lower concentration. Where the term "comprising" is used in the specification or clams, it is not intended to exclude any terms, steps or features not specifically recited. For the avoidance of doubt, the word "comprising" is intended to mean "including" but not necessarily "consisting of" or "composed of". In other words, the listed steps, options, or alternatives need not be exhaustive. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention relates to liquid compositions which contain fatty acid isethionate product, wherein the product contains 15 to 50%, preferably greater than or equal to 20% to 50% of free fatty acids/fatty soaps, and wherein greater than 50%, preferably greater than 60% of the free fatty acid/soaps in the product is chain length $C_{16}$ to $C_{20}$ and greater than or equal to 20%, preferably greater than 25% of the fatty acyl isethionate products are chain length $\geq C_{16}$. On the one hand, use of such product is beneficial because of its mildness and lather. On the other hand, it would be beneficial to obtain the benefits of the use of such products while minimizing costs by using less of the product. Using less, however, would be expected to result in weak foam values. Unexpectedly, applicants have found that less can be used, not by incorporating additional free fatty acid but, quite to the contrary, by keeping total amount of free fatty acid/fatty acid soap (from combined amounts of product and free fatty acid/soap in the composition) below defined critical values.

More specifically, the present invention relates to composition comprising:

(a) 0.3 to less than 4% by wt. fatty acyl isethionate product, wherein said product comprises 40 to 80% fatty acyl isethionate as well as 15 to 50%, preferably greater than or equal to 20% to 50% free fatty acids and/or fatty soaps in that product and wherein (e.g., to ensure mildness of final compositions), greater than 20%, preferably greater than 25% of fatty acyl isethionate are of chain length $\geq C_{16}$ and greater than 50%, preferably greater than 60% of free fatty acid/soap are of chain length $\geq C_{16}$ (e.g., $C_{16}$ to $C_{24}$, preferably $C_{16}$ to $C_{20}$);

(b) 3 to 15%, preferably 5 to 12% by wt. of a co-surfactant selected from the group consisting of anionic surfactant (excluding fatty acyl isethionate component of the fatty acyl isethionate product of (a)), amphoteric surfactant, nonionic surfactant, and mixtures thereof;

(c) 0.1 to less than 4% $C_8$ to $C_{20}$ total linear free fatty acids/fatty soap (comprising both free fatty acids/fatty soaps in fatty acid product (a) as well as those added separately in composition), wherein the total amount of linear $C_{16}$ to $C_{20}$ fatty acids is less than 2%, preferably less than 1.5%, and at least 0.1%, preferably 0.3%.

Preferably, the ratio of fatty acyl isethionate surfactant of item (a) to total synthetic surfactants in item (b) is less than ½, preferably less than ⅓.

Preferably, foam volume (measured by cylinder shake method) at fatty acid/soap level less than 4% is better by at least 10%, preferably about 15% relative to identical composition comprising greater than or equal to 4% total fatty acids/soap.

The pH of the composition is typically is from about 4.5 to 7.6, preferably 5.0 to 7.2.

Definition

For purposes of this invention, a fatty acyl isethionate "product" comprises (in addition to other components) both pure fatty acyl isethionate surfactant (e.g., 40 to 80%) as well as free fatty acid and/or fatty acid salt (e.g., 15 to 50%).

The compositions of the invention comprise 0.3, preferably 0.5 to less than 4% by wt. fatty acyl isethionate surfactant product comprising 40 to 80% fatty isethionate and 15%, possibly 20% minimum to 50% of free fatty acids/fatty soaps in that product. In addition, greater than 20%, preferably greater than 25% of the fatty acyl isethionate are of chain length $\geq C_{16}$ and greater than 50%, preferably greater than 60% of the free fatty acid/soap are of chain length $C_{16}$ to $C_{20}$.

Thus, for example, a product containing at least 15% fatty acids/soaps and greater than 50% $C_{16}$ to $C_{20}$ would have greater than 7.5% $C_{16}$ to $C_{20}$ fatty acid/soaps in the fatty acyl isethionate product.

Fatty acyl isethionate surfactant are typically prepared by the reaction of an isethionates salt such as alkali metal isethionates and an aliphatic fatty acid having 8 to 20 carbon atoms and Iodine Value (measuring degree of unsaturation) of less than 20 g, for example:

$$HOR^1SO_3M + RCOOH \rightarrow RCOOR^1SO_3H$$

where $R^1$ is an aliphatic hydrocarbon radical containing 2 to 4 carbons;
  M is alkali metal cation or metal ion (e.g., sodium, magnesium, potassium, lithium), ammonium or substituted ammonium cation or other counterion; and
  R is an aliphatic hydrocarbon radical having 7 to 24, preferably 8 to 22 carbons.

Depending on the processing conditions used, the resulting fatty acyl isethionate product can be a mixture of 40 to 80% by weight of fatty acyl isethionates and 50 to about 15 wt %, typically 40 to 20 wt % of free fatty acids, in addition to isethionates salts which are present typically at less than 5 wt %, and traces (less than 2 wt. %) of other impurities. Preferably, a mixture of aliphatic fatty acids is used for the preparation of commercial fatty acyl isethionates surfactants and resulting fatty acyl isethionate surfactants (e.g., resulting from reaction of alkali metal isethionate and aliphatic fatty acid) should have more than 20 wt %, preferably more than 25%, but no more than 40% wt., preferably 35% (on basis of fatty acyl isethionates reaction product) of fatty acyl group with 16 or greater carbon atoms to provide both lather and mildness of the resulting fatty acyl isethionate product. These longer chain fatty acyl isethionate surfactants and fatty acids, i.e. fatty acyl group and fatty acid with 16 or more carbons, form insoluble surfactant/fatty acid crystals typically in water at ambient temperatures. It is believed that these long chain fatty acyl isethionate surfactants together with free long chain fatty acids in the product contribute to the mildness of the fatty acyl isethionate product for skin cleanser applications.

Examples of commercial fatty acyl isethionate products that are particularly useful in the invention are DEFI flakes and Dove® cleansing bar noodles produced by Unilever. DEFI (Direct Esterification of Fatty Isethionate) flakes typically contain about 68 to 80 wt % of sodium fatty acyl isethionate and 15 to 30 wt % free fatty acid. More than 25 wt % and no more than 35% of fatty acyl group of the resulting fatty acyl isethionate have 16 to 18 carbon atoms; and more than 60wt % of the free fatty acid have 16 to 18 carbon atoms. Dove® cleansing bar noodles are mixtures of DEFI flakes described above and long chain (mainly $C_{16}$ and $C_{18}$) fatty acid and fatty soap which contain about 40 to 55 wt % of fatty acyl isethionate and 30 to 40 wt % of fatty acid and fatty soap. Due to high level of long chain (16 or more carbons) fatty acyl isethionate and fatty acid, these preferred fatty acyl isethionate surfactant products are extremely mild and have very good emollient benefits to the skin. DEFI flake and Dove® cleansing bar noodles are the mostly widely used fatty acyl isethionate products in personal cleansing market especially personal cleansing bar. Incorporation of these mild fatty acyl isethionate products into personal cleansing liquid and achieving excellent lathering properties of the resulting liquids are extremely desirable.

It was surprising to find that addition of such preferred fatty acyl isethionate product to a liquid containing synthetic cosurfactants (described below) as the main surfactant has a big impact on lather of the resulting liquids. This is shown in examples of this invention. At low level of the fatty acyl isethionate product, the lather of the liquid was enhanced due to addition of extra surfactant (Example 1 vs. comparative example E where lather range from 37.1 to 43.4 when using 2% of isethionate product within definition of invention). However, at a level of 4% (comparative example C), the lather unexpectedly decreased compared to the liquid without the fatty acyl isethionate product (comparative example E). A similar liquid prepared using Na cocoyl isethionate product (Jordopan CI) containing mainly short chain fatty acyl isethionate surfactant and low level (5-8%) of coco fatty acid did not show such negative effect on lather (comparative example C vs. $C_2$). However, especially given low levels of $>C_{16}$ total fatty acids and fatty acyl isethionate surfactant, such composition would be less mild. To both achieve mildness and maintain or enhance lather of liquids containing low level of synthetic surfactants, the amount of the preferred fatty acyl isethionate product added to the liquid composition of this invention is lower than 4wt %, preferably lower than 3 wt %.

Synthetic Co-Surfactants

A second component of the subject invention are surfactants selected from the groups consisting of anionic surfactants, nonionic surfactants, zwitterionic surfactants, amphoteric surfactants as described below. When determining level of co-surfactant, the amount of acyl isethionate surfactant formed as part of the acyl isethionate product is not counted. The amount of synthetic co-surfactant used in the present invention can be in the range of 3 to 15%, preferably 5 to 12 wt %; and its level is more than the amount of fatty acyl isethionate product added to the liquid of the invention. The ratio of synthetic co-surfactant to fatty acyl isethionate surfactant is at least 2 to 1, preferably at least 3 to 1 and no more than 20 to 1.

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

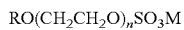
$$RO(CH_2CH_2O)_nSO_3M$$

wherein R is an alkyl or alkenyl having 8 to 18 carbons, preferably 12 to 16 carbons, n has an average value of greater than at least 0.5, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, alkyl and acyl glycinates, alkyl sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and branched acyl isethionates.

Another class of anionics are ethoxylated carboxylates such as follows:

wherein R is $C_8$ to $C_{20}$ alkyl; n is 1 to 20; and M is as defined above.

Another carboxylate which can be used is amido alkyl polypeptide carboxylates such as, for example, Monteine LCQ® by Seppic. Soap, i.e. neutralized fatty acid, is not considered as synthetic cosurfactant in this invention.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

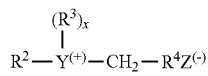

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

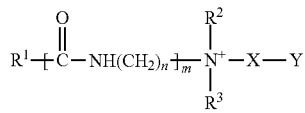

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$ Amphoacetates and diamphoacetates are also intended to be covered in possible zwitterionic and/or amphoteric compounds which may be used.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

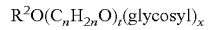

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Other surfactants which may be used are described in U.S. Pat. No. 3, 723,325 to Parran Jr. and "Surface Active Agents and Detergents" (Vol. I & II) by Schwartz, Perry & Berch, both of which is also incorporated into the subject application by reference.

One preferred composition of the invention comprises acyl isethionate product with mixture of anionic (e.g., alkoxylated sulfate such as alkali metal alkyl ether sulfate) and amphoteric (e.g., betaine). Another preferred embodiment includes isethionate product and anionic which comprises mixtures of sulfate and glycinate surfactants in combination with amphoteric. In other embodiments, the isethionate product may be used with alkyl ether sulfate alone; with amphoteric alone or with no co-surfactant at all.

Fatty Acids

Another essential ingredient of the present invention is combination of long chain and short chain linear fatty acids/fatty soaps in the liquid composition. For ease of discussion, it is noted that whenever the term fatty acid is used, it will be understood to encompass both fatty acid and fatty acid soaps. Long chain fatty acid in this invention is defined as linear fatty acid with 16 to 20 carbons; and short chain fatty acid is linear fatty acid with 8 to 14 (preferably 10 to 12) carbons. Fatty acids are used to increase the viscosity of the liquid composition at or above ambient temperature such that the viscosity of the liquid composition remains viscous enough to maintain its physical stability when stored at or above room temperature. Besides increasing the liquid viscosity and storage stability, linear long chain fatty acids have good emollient properties and can enhance the mildness of synthetic surfactants. Linear short chain fatty acids especially $C_{10}$ to $C_{12}$, are known to be effective to enhance the lather of a liquid composition. Mixture of long chain and short chain fatty acids is desired to make liquid which is stable, has good lather and is mild to the skin. For the liquid composition of this invention containing both low level of the preferred mild fatty acyl isethionate products and synthetic cosurfactants, it was found that a specific fatty acid mixture is required to achieve good lathering properties of the liquids. As shown in the examples of this invention, to have good lather the total amount of fatty acids has to be less than 4%, preferably less than 3.5%; and linear fatty acid with 16 or more carbons has to be less than 2.0%, preferably less than 1.5% and most preferably less than 1.0% in the total liquid composition of this invention. The minimum amount of long chain fatty acids depends on the level of fatty acyl isethionate product in the liquid composition and its fatty acid content; it is preferred to have at least 0.1%, preferably 0.3% to achieve good lather and mildness.

Water Soluble/Dispersible Polymers

Water soluble/dispersible polymers are an optional ingredient that is preferred to be included in the liquid composition of the invention. The water soluble/or dispersible polymer can be cationic, anionic, amphoteric or nonionic polymer with molecular weight higher than 100,000 Dalton. These polymers are known to increase the viscosity and stability of liquid cleanser compositions, to enhance in-use and after-use skin sensory feels, and to enhance lather creaminess and lather stability. When water insoluble skin benefit agent is used in this invention, the water soluble/dispersible polymers are required to stably suspend the added skin benefit agents. Amount of polymers used can be in the range of 0.1 up to 10 wt % depending on the composition of the liquid cleansers.

Examples of water soluble/or dispersible polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum arabic, gum acacia, gum agar, xanthan gum and mixtures thereof; modified and nonmodified starch granules with gelatinization temperature between 30 to 85° C. and pregelatinized cold water soluble starch; polyacrylate; Carbopols; alkaline soluble emulsion polymer such as Aculyn 28, Aculyn 22 or Carbopol Aqua SF1; cationic polymer such as modified polysaccharides including cationic guar available from Rhone Poulenc under the trade name Jaguar C13S, Jaguar C14S, Jaguar C17, or Jaguar C16, BF Guar C-17 from Lamberti; Aqua D4091 and D4051 from Aqualon; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrosoft Um-200; and Polyquaternium-24.

Gel forming polymers such as modified or non-modified starch granules, xanthan gum, Carbopol, alkaline-soluble emulsion polymers and cationic guar gum such as Lamberti BF Guar C17, and cationic modified cellulose such as UCARE Polymer JR 30 or JR 40 are particularly preferred for this invention.

Water Soluble Skin Benefit Agents

Water-soluble skin benefit agents another optional ingredient that is preferred to be included in the liquid compositions of the invention. A variety of water-soluble skin benefit agents can be used and the level can be from 0 to 50 weight %, preferably 1 to 30%. The materials include, but are not limited to, polyhydroxy alcohols such as glycerin, propylene glycol, dipropylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerin, sorbitol and propylene glycol.

The liquid cleansing composition of the invention also may comprise 0 to 40% by wt. benefit agent.

One class of ingredients are nutrients used to moisturize and strengthen, for example, the skin. These include:
 a) vitamins such as vitamin A and E, and vitamin alkyl esters such as vitamin C alkyl esters;
 b) lipids such as cholesterol, cholesterol esters, lanolin, creaminess, sucrose esters, and pseudo-ceramides;
 c) liposome forming materials such as phospholipids, and suitable amphophilic molecules having two long hydrocarbon chains;
 d) essential fatty acids, poly unsaturated fatty acids, and sources of these materials;
 e) triglycerides of unsaturated fatty acids such as sunflower oil, primrose oil avocado oil, almond oil;
 f) vegetable butters formed from mixtures of saturated and unsaturated fatty acids such as Shea butter;
 g) minerals such as sources of zinc, magnesium, and iron;

A second type of skin benefit agent is a skin conditioner used to provide a moisturized feel to the skin. Suitable skin conditioners include:
 a) silicone oils, gums and modifications thereof such as linear and cyclic polydimethylsiloxanes, amino, alkyl, and alkyl aryl silicone oils;
 b) hydrocarbons such as liquid paraffins, petrolatum, Vaseline, microcrystalline wax, ceresin, squalene, pristan, paraffin wax and mineral oil;
 c) conditioning proteins such as milk proteins, silk proteins and glutens;
 d) cationic polymers as conditioners which may be used include Quatrisoft LM-200 Polyquaternium-24, Merquat Plus 3330-Polyquaternium 30; and Jaguar® type conditioners;
 e) humectants such as glycerol, sorbitol, and urea;
 f) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:
 a) antimicrobials such as 2-hydrozy-4,2',4'-trichlorodiphenylether (DP300) 2,6-dimethyl-4-hydroxychlorobenzene (PCMX),3,4,4'-trichlorocarbanilide (TCC), 3-trifluoromethyl-4,4'-dichlorocarbanilide (TFC), benzoyl peroxide, zinc salts, tea tree oil,
 b) anti-acne agents such as salicylic acid, lactic acid, glycolic acid, and citric acid, and benzoyl peroxide (also an antimicrobial agent),
 c) oil control agents including sebum suppressants, modifiers such as silica, titanium dioxide, oil absorbers, such as micro sponges, d) astringents including tannins, zinc and aluminum salts, plant extracts such as from green tea and Witch-hazel (Hammailes),
e) scrub and exfoliating particles, such as polyethylene spheres, agglomerated silica, sugar, ground pits, seeds, and husks such as from walnuts, peach, avocado, and oats, salts,
f) cooling agents such as methanol and its various derivatives and lower alcohols,
g) fruit and herbal extracts,
h) skin calming agents such as aloe vera,
i) essential oils such as mentah, jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geranoil, evening primrose, camphor, tymol, spirantol, penene, limonene and terpenoid oils.

Other benefit agents that can be employed include antiaging compounds, sunscreens, and in lightening agents.

When the benefit agent is oil, especially low viscosity oil, it may be advantageous to pre-thicken it to enhance its delivery. In such cases, hydrophobic polymers of the type describe in U.S. Pat. No. 5,817,609 to He et al. may be employed, which is incorporated by reference into the subject application.

The final liquid cleanser composition of the present invention should have a viscosity more than 10,000 cps preferably greater than 20,000 cps and less than 500,000 cps measured at 0.5 rpm using Brookfield RVT Viscometer with Helipath Accessory; chuck, weight and closer assembly for T-bar Spindle A attachment and a plastic cups diameter greater than 2.5 inches at temperature 25° C.;

and pH of the liquid should be between 4.5 to 7.6, preferably 5.0 to 7.2. The compositions should also be physically phase stable at room temperature and 40° C. for at least two 2 weeks.

Other Optional Components

In addition, the compositions of the invention may include 0 to 10% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, $T^1O_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenyl ether (DP300); preservatives such as dimethyloldimethylhydantoin (Glydant XL 1000), parabens, sorbic acid etc.

Antioxidants such as, for example, butylated hydroxytoluene (BHT) may be used advantageously in amounts of about 0.01% or higher if appropriate.

Polyethylene glycols as conditioners which may be used include:

| Polyox | WSR-25 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

Foaming by Solution Cylinder Shake Method:

1. Mix 5 g of the liquid cleanser with 45 g of deionized water for about 5 minutes until it forms a uniform solution.
2. Add 10 grams of the above diluted liquid cleanser solution to a 50 cc cylinder (about 24 cm high, 2.06 cm in diameter).
3. Cap the cylinder with glass stopper, grape the top of the cylinder and shake the cylinder in a up and down motion with a distance about 20 to 30 cm 20 times within 8 to 12 sec.
4. Once shaking is over, wait 60 seconds before taking the foam measurement.
5. Measure the foam volume, which is defined as the volume from the surface of the solution to the top of the foam column.
6. Repeat the run for total 4 times, the average foam volume with standard deviation for each liquid is calculated and shown in the tables.

EXAMPLES 1-3 AND COMPARATIVE EXAMPLES

The following examples 1 to 3 and comparatives A to E were prepared to demonstrate the invention.

|  | Example of this invention |  |  |  |  |  |  |  |  |  |
| --- | --- | --- | --- | --- | --- | --- | --- | --- | --- | --- |
|  | 1 | 2 | 3 | — | — | — | — | — | — | — |
|  |  |  |  | Comparative example |  |  |  |  |  |  |
|  | — | — | — | A | B | C | C2 | D | E | F (Control) |
| Isethionate product A | 2 | 2 | 2 | 2 | 2 | 4 | — | 2 | 2 | — |
| Na cocoyl isethionate Jordapon CI | — | — | — | — | — | — | 4 | — | — | — |
| Na cocoamido propyl betaine | 4 | 4 | 4 | 4 | 4 | 4 | 4 | 4 | 4 | 4 |
| Na cocoyl glycinate | 2.5 | 2.5 | 2.5 | 2.5 | 2.5 | 2.5 | 2.5 | 2.5 | 2.5 | 2.5 |
| Na laurylethoxyl sulfate | 3.5 | 3.5 | 3.5 | 3.5 | 3.5 | 3.5 | 3.5 | 3.5 | 3.5 | 3.5 |
| Lauric acid | 1.5 | 0.81 | — | 2.3 | 2.9 | 1.5 | 1.5 | 4.0 | 0.5 | 1.5 |
| ASAD* | — | 0.69 | — | 1.0 | 0.4 | — | — | 0 | 1.0 | — |
| Glycerin | 1.15 | 1.15 | 1.15 | 1.15 | 1.15 | 1.15 | 1.15 | 1.15 | 1.15 | 1.15 |
| Cationic polymer Aqua D4051 | 0.2 | 0.2 | 0.2 | 0.2 | 0.2 | 0.2 | 0.2 | 0.2 | 0.2 | 0.2 |

-continued

|  | Example of this invention | | | Comparative example | | | | | | | F (Control) |
|---|---|---|---|---|---|---|---|---|---|---|---|
|  | 1 | 2 | 3 | — | — | — | — | — | — | — | — |
|  | — | — | — | A | B | C | C2 | D | E | F (Control) |  |
| Sunflower seed oil | 1 | 1 | 1 | 1 | 1 | 1 | 1 | 1 | 1 | 1 |
| Petrolatum Penreco Snow | 4 | 4 | 4 | 4 | 4 | 4 | 4 | 4 | 4 | 4 |
| Pure Gel B990 starch | 4 | 6 | 8 | 4 | 4 | 4 | 4 | 4 | 4 | 4 |
| Perfume | 1.5 | 1.5 | 1.5 | 1.5 | 1.5 | 1.5 | 1.5 | 1.5 | 1.5 | 1.5 |
| Total fatty acid/fatty soaps | 2.25 | 2.25 | 0.70 | 4.05 | 4.05 | 2.9 | 1.74 | 4.70 | 2.25 | 1.5 |
| Total fatty acid/fatty soaps greater than or equal to $C_{16}$ wt. % | 0.55 | 1.24 | 0.55 | 1.55 | 0.95 | 1.10 | 0.096 | 0.55 | 1.55 | 0 |
| Lather volume (cc) by Solution Cylinder Shake Method | | | | | | | | | | |
| Foam volume (cc) | 42.5 | 41.4 | 40.1 | 23.5 | 30.0 | 33.3 | 42.5 | 28.5 | 37.3 | 38 |
|  | 44.5 | 42.5 | 40.4 | 24.7 | 29.4 | 30.8 | 41 | 28.2 | 37.4 | 35.5 |
|  | 41.5 | 43.6 | 41 | 22.7 | 25.8 | 30.2 | 44.5 | 26.4 | 36.7 | 36.5 |
|  | 45.0 | 40.5 | 43.1 | 25.0 | 27.9 | 31.2 | 40.5 | 25.2 | 37.0 | 38.5 |
| Average foam volume (cc) | 43.4 | 42 | 41.2 | 23.9 | 28.3 | 31.4 | 41.1 | 27.1 | 37.2 | 37.1 |
| Standard deviation (cc) | 1.37 | 1.05 | 0.98 | 0.87 | 1.43 | 0.96 | 1.37 | 1.28 | 0.3 | 1.1 |

ASAD: Mixture of 51% $C_{18}$/49% $C_{16}$ linear fatty acid.

The following examples 4-7 and comparatives G-J were further prepared to demonstrate the invention.

|  | Example of this invention | | | | | | | |
|---|---|---|---|---|---|---|---|---|
|  | 4 | — | 5 | — | 6 | 7 | — | — |
|  | Comparative example | | | | | | | |
|  | — | G | — | H | — | — | I | J |
| Isethionate product A | 2 | 2 | 1 | 1 | 2 | 2 | 2 | 2 |
| Na cocoamido propyl betaine | 0 | 0 | 4.8 | 4.8 | 4.8 | 4.8 | 4.8 | 4.8 |
| Na cocoyl glycinate | 2.7 | 2.7 | 4 | 4 | 4 | 4 | 4 | 4 |
| Na laurylsarcosinate | — | — | 1 | 1 | 1 | 1 | 1 | 1 |
| Na laurylethoxyl sulfate | 5.0 | 5.0 | — | — | — | — | — | — |
| Lauric acid | 2.5 | 2.5 | 1.6 | 3.1 | 3.0 | 2.0 | 3.0 | 1.5 |
| ASAD* | — | 0.8 | 0 | 0.6 | — | — | 0.6 | 1.5 |
| Glycerin | 1.15 | 1.15 | 10 | 10 | 6 | 6 | 6 | 6 |
| Cationic polymer Lamberti BF Guar C17 | — | — | 0.4 | 0.4 | 0.2 | 0.2 | 0.2 | 0.2 |
| Sunflower seed oil | 1 | 1 | — | — | — | — | — | — |
| Petrolatum Penreco Snow | 4 | 4 | 30 | 30 | 5 | 5 | 5 | 5 |
| Pure Gel B990 starch | — | — | 6 | 3 | 6 | 6 | 6 | 6 |
| Carbopol C980 | 0.8 | 0.8 | — | — | — | — | — | — |
| Perfume | 1.3 | 1.3 | 1.0 | 1.0 | 1 | 1 | 1 | 1 |
| Total fatty acid/fatty soaps | 3.25 | 4.05 | 1.95 | 4.05 | 3.70 | 2.70 | 4.30 | 3.70 |
| Total fatty acid/fatty soaps greater than or equal to $C_{16}$ | 0.55 | 1.35 | 0.28 | 0.88 | 0.55 | 0.55 | 1.15 | 2.05 |
| Lather volume (cc) by Solution Cylinder Shake Method | | | | | | | | |
|  | 41.0 | 27.5 | 48.0 | 36.2 | 43.0 | 46.5 | 28.1 | 34.0 |
|  | 41.7 | 24.9 | 43.5 | 32.8 | 43.0 | 45.0 | 28.0 | 34.7 |
|  | 38.5 | 25.8 | 44.5 | 36.0 | 44.5 | 42.5 | 26.3 | 32.2 |
|  | 37.0 | 27.8 | 46.2 | 34.0 | 44.5 | 44.5 | 31.5 | 34.1 |
| Average foam volume | 39.6 | 26.5 | 45.6 | 34.8 | 43.7 | 44.6 | 28.5 | 33.7 |
| Standard deviation | 1.8 | 1.15 | 1.55 | 1.35 | 0.75 | 1.13 | 1.51 | 0.78 |

ASAD: Mixture of 51% C18/49% C16 linear fatty acid.

Discussion

All examples in Table 1 and Table 2 were prepared by mixing all the ingredients except petrolatum, sunflower seed oil, perfume, glydant and EDTA at 70 to 75° C. for 30 to 50 minutes until all the solid ingredients such as isethionate product A and fatty acids dissolved to form an uniform mixture. Molten petrolatum and sunflower seed oil were added during cooling. Perfume and glydant plus (a hydantoin preservative) were added after the liquid was cooled below 40° C. Isethionate product A are fatty acyl isethionate products manufactured by Unilever. They contain about 50 wt % of fatty acyl isethionate surfactant with about 30% of the fatty acyl group equal to or longer than 16 carbon, and about 35 wt % of linear fatty acid/linear fatty soap in which about 79 wt % of the fatty acid/fatty soap have 16 to 20 carbons. The lather volume for each prepared sample measured using the solution shake method as set forth in the protocol is also summarized in Tables 1 and 2.

Comparative example F (Control), a liquid without any fatty acyl isethionate product, was prepared as control for lather volume comparison. It can be seen clearly in Examples 1, 2 and 3 versus comparative F that addition of fatty acyl isethionate product at low level (2% isethionate product A) enhances foam volume (e.g., from 37.1 to about 42 on average). However, when higher level, i.e. 4%, of the preferred fatty acyl isethionate product is added (Comparative example C), foam volume is depressed (31.4) compared to comparative F which contains no fatty acyl isethionate product. This happens only for the preferred fatty acyl isethionate product of this invention. Addition of 4% Jordapon, Na cocoyl isethionate product containing about 6% free coconut fatty acid and about 85% of fatty acyl isethionate surfactant with about 18% of the fatty acyl group equal to or longer than 16 carbons, shows an enhancement of foam volume as shown in comparative C2. However, since $C_2$ has less % of $>C_{16}$ fatty acid and fatty acyl isethonate, it would not have good mildness.

Again, comparing Examples 3, 4, 5 and 6 to Comparatives G, H, I and J, it is seen that keeping total fatty acid/fatty soap level low (<4%) is critical. In all inventive examples, foam (at >40 cc absolute values) is significantly better.)

What is claimed is:

1. A personal liquid cleansing composition comprising:
   (a) 0.3 to less than 4% by wt. fatty acyl isethionate product comprising 40 to 80% fatty acyl isethionate and 15% to 50% free fatty acid and/or soap wherein greater than 20% of the fatty acyl isethionate are of chain length greater than or equal to $C_{16}$ and greater than 50% of the free fatty acid/soap is of chain length greater than or equal to $C_{16}$ to $C_{24}$;
   (b) 3 to 15% by wt. of a co-surfactant selected from the group consisting of anionic surfactant, amphoteric surfactant, nonionic surfactant, and mixtures thereof wherein said anionic surfactant excludes fatty acyl isethionate product of (a);
   (c) 0.1 to less than 4% $C_8$ to $C_{20}$ total linear free fatty acids/fatty soap wherein said total linear free fatty acids/fatty soap includes both free fatty acids/fatty soaps of fatty acyl isethionate product (a) as well as those added separately in composition;
   wherein total amount of linear $C_{16}$ to $C_{20}$ fatty acids is less than 1.5%, but is at least 0.1% by wt; and
   wherein the ration of fatty acyl isethionate surfactant of (a) to total synthetic surfactant (b) is less than 1 to 2; wherein foam value of composition (measured by cylinder shake shake method with total fatty acid/soap level less than 4% is better by at least 10%, relative to identical composition comprising greater than or equal to 4% total fatty acids/soap.

2. A composition according to claim 1 having pH of 4.5 to 7.6.

* * * * *